United States Patent [19]

Lin et al.

[11] 4,211,726
[45] Jul. 8, 1980

[54] SYNTHESIS OF SUBSTITUTED 9,10-ANTHRACENE-DICARBOXALDEHYDES AND 9,10-DIHYDRO-9,10-ANTHRACENEDICARBOXALDEHYDES

[75] Inventors: Yang-I Lin, Nanuet; Stanley A. Lang, Jr., Stony Point, both of N.Y.

[73] Assignee: American Cyanamid Company, Stamford, Conn.

[21] Appl. No.: 12,678

[22] Filed: Feb. 16, 1979

[51] Int. Cl.$^2$ .................................................. C07C 45/00
[52] U.S. Cl. ..................................... 568/424; 260/578; 260/556 C; 260/348.17; 568/433; 568/430
[58] Field of Search ................... 260/599, 578, 556 C, 260/600 R

[56] References Cited

U.S. PATENT DOCUMENTS

| 3,442,949 | 5/1969 | Wendler | 260/599 X |
| 3,641,058 | 2/1972 | Corrigan et al. | 260/599 X |
| 3,891,712 | 6/1975 | Fried et al. | 260/599 |
| 3,901,896 | 8/1975 | Albright | 260/599 X |
| 4,000,131 | 12/1976 | Rosenberger et al. | 260/599 X |

FOREIGN PATENT DOCUMENTS 1331281  5/1963  France ................................. 260/599

Primary Examiner—Bernard Helfin
Attorney, Agent, or Firm—Edward A. Conroy, Jr.

[57] ABSTRACT

There is provided a process for the manufacture of substituted 9,10-anthracenedicarboxaldehydes and substituted 9,10-dihydro-9,10-anthracenedicarboxaldehydes useful as intermediates in the preparation of antibacterial agents.

2 Claims, No Drawings

SYNTHESIS OF SUBSTITUTED 9,10-ANTHRACENE-DICARBOXALDEHYDES AND 9,10-DIHYDRO-9,10-ANTHRACENEDICARBOX-ALDEHYDES

BRIEF SUMMARY OF THE INVENTION

The present invention relates to a novel multistep process for the preparation of substituted 9,10-anthracenedicarboxaldehydes and the 9,10-dihydro derivatives thereof from the corresponding substituted anthraquinones. The products of the novel process of the present invention are useful as starting materials for the preparation of antibacterial agents as set forth in the copending applications for U.S. Letters Patent to Murdock et al., Ser. No. 939,591, Child et al., Ser. No. 943,908, and Child et al., Ser. No. 947,976, which are hereby incorporated by reference. The novel process of the present invention may be illustrated by the following reaction scheme:

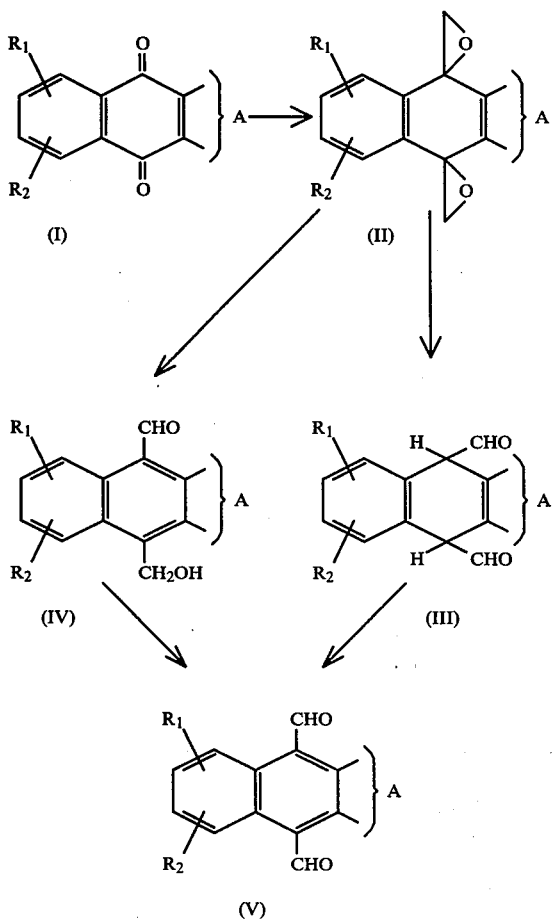

wherein A is a divalent moiety selected from the group consisting of those of the formulae:

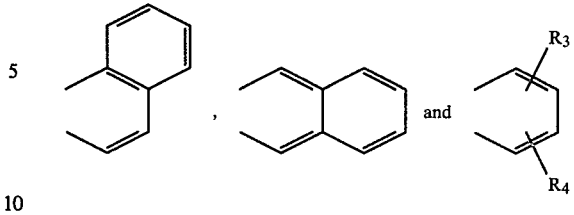

and $R_1$, $R_2$, $R_3$ and $R_4$ are each individually selected from the group consisting of hydrogen, halogen (F, Cl, Br, I), hydroxy, nitro, amino, sulfonamido, alkyl having up to 4 carbon atoms and alkoxy having up to 4 carbon atoms.

DETAILED DESCRIPTION OF THE INVENTION

In accordance with the above reaction scheme, a solution of trimethylsulfonium iodide in dimethylsulfoxide is added dropwise (over 15–45 minutes and at room temperature) to a stirred mixture of sodium hydride and an appropriately substituted anthraquinone (I) in dimethylsulfoxide, in the dark, under an inert atmosphere such as argon or nitrogen. After stirring for an addition 1–2 hours at room temperature, the reaction mixture is poured into ice water and the crystals of the corresponding dispiro[oxirane-2,9'(10'H)-anthracene-10',2"oxirane] (II) which separate are collected. This addition reaction has been described by T. J. McCarthy et al., Synthetic Communication 8(6), 379–382 (1978). The rearrangement of the dispiro derivatives (II) to the corresponding 9,10-dihydro-9,10-anthracenedicarboxaldehydes (III) is accomplished with boron trifluoride, magnesium bromide, trifluoroacetic acid, methanesulfonic acid and the like in an aprotic organic solvent such as diethyl ether, benzene, tetrahydrofuran, dioxane, etc. This rearrangement is best carried out at −45°–0° C. for a period of 5–15 minutes in the presence of base such as potassium carbonate, soda ash, and the like. Filtration and workup of the reaction mixture followed by removal of the solvent from the filtrate in vacuo provides the product (III) as crystals. The dispiro derivatives (II) may also be rearranged to the corresponding 9-formyl-10-hydroxymethylanthracenes (IV) with lithium bromide, lithium perchlorate, boron trifluoride, magnesium bromide, trifluoroacetic acid, methanesulfonic acid, and the like in an aprotic organic solvent such as acetonitrile, benzene, etc. This rearrangement is best carried out at 25°–75° C. in the dark for a period of 10–20 hours. Filtration of the reaction mixture followed by cooling of the filtrate to −40° C. in a dry-ice/acetone bath results in crystallization of the product (IV).

The oxidation of the 9,10-dihydro-9,10-anthracenedicarboxaldehydes (III) and the 9-formyl-10-hydroxymethylanthracenes (V) to the corresponding 9,10-anthracenedicarboxaldehydes (V) is accomplished by treating (III) or (IV) with a 2 to 8 mole equivalent of an oxidizing agent selected from the group consisting of lead tetraacetate, nickel peroxide, manganese oxide, chromium trioxide, selenium dioxide, o-chloranil, dichlorodicyano-1,4-benzoquinone, dimethylsulfoxide and diethylazodicarboxylate. These oxidations are best carried out at a temperature between 0° C. and 100° C. and preferably from about 20° C. to about 60° C. in a solvent consisting of aqueous solutions of acetic acid, acetonitrile, tetrahydrofuran, dioxane, dimethoxyethane, dimethylsulfoxide, diethylene glycol dimethyl ether or dimethylformamide which may also contain oxygen, nitric acid, perchloric acid or phosphoric acid for a period of one to 24 hours. A preferred procedure for oxidizing (IV) to (V) consists of treating (IV) with sulfur trioxide-pyridine complex in anhydrous dimethylsulfoxide as solvent in the presence of triethylamine at room temperature (15°–40° C.) for a period of half an hour to several hours. A preferred procedure for oxidizing (III) to (V) consists of stirring (III) in a solution of lithium bromide in acetonitrile saturated with oxygen at 50°–75° C. for 12–24 hours. In every case, the isolation and purification of the 9,10-anthracenedicarboxaldehydes (V) is achieved by routine procedure such as filtration, concentration, extraction, chromatography, crystallization, etc. well known in the art.

The invention will be described in greater detail in conjunction with the following specific examples.

EXAMPLE 1

Dispiro[oxirane-2,9'(10'H)-anthracene-10',2''-oxirane]

A solution comprising 41.26 g. of trimethylsulfonium iodide in 340 ml. of dry dimethylsulfoxide is added dropwise, over 30 minutes, to a stirred mixture of 9.72 g. of sodium hydride (50% oil dispersion) and 18.7 g. of anthraquinone in 560 ml. of dimethylsulfoxide, in the dark, under argon. The mixture is stirred for an additional hour and filtered through a sintered glass funnel. The filtrate is poured into 1500 ml. of ice-water and allowed to stand for 20 minutes. The crystals are collected and washed with water and cold methanol, giving 20.2 g. of the desired product as colorless crystals, m.p. 119°–121° C.

EXAMPLE 2

9,10-Dihydro-9,10-anthracenedicarboxaldehyde

A mixture of 0.1 ml. of boron trifluoride etherate in 40 ml. of ether and 2.0 g. of potassium carbonate is stirred at 0° C. for 10 minutes. A solution of 500 mg. of dispiro[oxirane-2,9'(10'H)-anthracene-10',2''-oxirane] in 20 ml. of ether is added. The resulting mixture is stirred at 0° C. for an additional 2 minutes, and filtered. The ether filtrate is washed twice with a mixture of 10 ml. of saturated sodium bicarbonate solution and 10 ml. of ice-water, then dried over anhydrous sodium sulfate and filtered. The ether is removed and the residue is recrystallized from ether/hexane to give 384 mg. of the desired product as yellow crystals, m.p. 132°–135° C.

EXAMPLE 3

10-Hydroxymethyl-9-anthracenecarboxaldehyde

To a solution of 4.0 g. of lithium bromide in 150 ml. of acetonitrile is added 2.36 g. of dispiro[oxirane-2,9'(10'H)-anthracene-10',2''-oxrane]. The mixture is stirred at 60° C., in the dark for 16 hours and then cooled to −40° C. in a dry-ice acetone bath. The resulting crystals are collected by filtration and washed with water, giving 2.2 g. of the desired product as yellow crystals, mp. 182°–184° C.

EXAMPLE 4

9,10-Anthracenedicarboxaldehyde

To a solution of 1.20 g. of 10-hydroxymethyl-9-anthracenecarboxaldehyde in a mixture of 14 ml. of triethylamine and 20 ml. of dry dimethylsulfoxide is added a solution of 4.80 g. of sulfur trioxide pyridine complex in 25 ml. of dry dimethylsulfoxide. The mixture is stirred for 50 minutes and then poured into 200 ml. of water. The crystals are collected and washed with water, giving 1.18 g. of the desired product as orange crystals, mp. 224°–245° C.

EXAMPLE 5

2'-Methyl-despiro[oxirane-2,9'(10'H)-anthracene-10',2''-oxirane]

A solution comprising 41.26 g. of trimethylsulfonium iodide in 340 ml. of dry dimethylsulfoxide is added dropwise over 30 minutes, to a stirred mixture of 9.72 g. of sodium hydride (50% oil dispersion) and 20.0 g. of 2-methylanthraquinone in 560 ml. of dry dimethylsulfoxide, in the dark, under argon. The mixture is stirred for an additional hour and filtered through a sintered glass funnel. The filtrate is poured into water and allowed to stand in a cold room for three hours. The crystals are collected and washed with water and cold methanol, giving 21.2 g. of the desired product as tan crystals, mp. 78°–81° C.

EXAMPLE 6

10-(Hydroxymethyl)-2(and 3)-methyl-9-anthraldehyde

To a solution of 16.0 g. of lithium bromide in 600 ml. of acetonitrile is added 10.0 g. of 2'-methyldispiro[oxirane-2,9'(10'H)-anthracene-10',2''-oxirane]. The mixture is stirred at 60° C. for 18 hours, filtered and the filtrate is concentrated to about 300 ml. and cooled to −40° C. in a dry ice-acetone bath. The solid is collected by filtration and washed with water giving 6.9 g. of the product as yellow crystals, mp. 110°–123° C. The acetonitrile is removed from the filtrate under reduced pressure, the residue is washed with water and recrystallized from acetonitrile, giving 1.3 g. of additional product as yellow crystals, mp. 110°–123° C.

EXAMPLE 7

2-Methyl-9,10-anthracenedicarboxaldehyde

To a solution of 1.25 g. of 10-(hydroxymethyl)-2-methyl-9-anthraldehyde in a mixture of 14 ml. of triethylamine and 20 ml. of dry dimethylsulfoxide is added a solution of 4.80 g. of sulfur trioxide pyridine complex in 20 ml. of dry dimethylsulfoxide. The reaction mixture is stirred for one hour and then poured into 200 ml. of water. The solid is collected and washed with water, giving 1.18 g. of the desired product as orange crystals, mp. 150°–152° C.

EXAMPLE 8

1'-Chloro-dispiro[oxirane-2,9'(10'H)-anthracene-10',2''-oxirane]

A solution comprising 41.26 g. of trimethylsulfonium iodide in 340 ml. of dry dimethylsulfoxide is added dropwise over 30 minutes, to a stirred mixture of 9.72 g. of sodium hydride (50% oil dispersion) and 21.9 g. of 1-chloroanthraquinone in 560 ml. of dry dimethylsulfoxide. The reaction proceeds as described in Example 5, giving 19.3 g. of the desired product as tan crystals, mp. 85°–92° C.

EXAMPLE 9

1(and 4)-Chloro-10-(hydroxymethyl)-9-anthraldehyde

To a solution of 16.0 g. of lithium bromide in 600 ml. of acetonitrile is added 10.0 g. of 1'-chloro-dispiro[oxirane-2,9'(10'H)-anthracene-10',2''-oxirane]. The reaction proceeds as described in Example 6, giving a total of 9.0 g. of the desired product as yellow crystals, mp. 133°–140° C.

EXAMPLE 10

1-Chloro-9,10-anthracenedicarboxaldehyde

To a solution of 1.35 g. of 1(and 4)-chloro-10-hydroxymethyl-9-anthraldehyde in a mixture of 14 ml. of triethylamine and 20 ml. of dry dimethylsulfoxide is added 4.8 g. of sulfur trioxide pyridine complex in 25 ml. of dry dimethylsulfoxide. The reaction proceeds as described in Example 7, giving 1.29 g. of the desired product as yellow crystals, mp. 186°–189° C.

EXAMPLE 11

2'-Chloro-dispiro[oxirane-2,9'(10'H)-anthracene-10',2''-oxirane]

A solution comprising 41.26 g. of trimethylsulfonium iodide in 340 ml. of dry dimethylsulfoxide is added dropwise over 30 minutes, to a stirred mixture of 9.72 g. of sodium hydride (50% oil dispersion) and 21.9 g. of 2-chloroanthraquinone in 560 ml. of dry dimethylsulfoxide, in the dark, under argon. The mixture is stirred for an additional hour and filtered through a sintered glass funnel. The filtrate is poured into 1500 ml. of ice-water and extracted three times with ether. The ether extracts are combined, washed with water, dried over sodium sulfate and evaporated, giving 23.2 g. of the desired product as a light yellow solid, mp. 61°–67° C.

EXAMPLE 12

2(and 3)-Chloro-10-(hydroxymethyl)-9-anthraldehyde

To a solution of 32.0 g. of lithium bromide in 1200 ml. of acetonitrile (dried over 3 Å molecular sieves) is added 23.2 g. of 2'-chloro-dispiro[oxirane-2,9'(10'H)-anthracene-10',2''-oxirane]. The reaction mixture is stirred at 60° C. for 20 hours and then cooled in a dry ice-acetone bath. The precipitate formed is collected by filtration and washed with water, yielding 21.1 g. of the product as yellow crystals, mp. 178°–180° C.

EXAMPLE 13

2-Chloro-9,10-anthracenedicarboxaldehyde

To a solution of 2.70 g. of 2(and 3)-chloro-10-(hydroxymethyl)-9-anthraldehyde in a mixture of 28.0 ml. of triethylamine and 40 ml. of anhydrous dimethylsulfoxide is added a solution of 9.6 g. of sulfur trioxide pyridine complex in 50 ml. of anhydrous dimethylsulfoxide. The reaction mixture is stirred at room temperature for one hour and then poured into 400 ml. of water. The product is collected by filtration and washed with water, giving 2.55 g. of the product as orange crystals, mp. 192°–195° C.

EXAMPLE 14

10-(Hydroxymethyl)-9-anthracenecarboxaldehyde

To a solution of 500 mg. of the product of Example 1 in 50 ml. of anhydrous ether maintaining at −45° C. is added dropwise a solution of 0.060 ml. of boron trifluoride in 2.0 ml. of anhydrous ether. The reaction mixture is stirred at −45° C. for 10 minutes and then allowed to warm to −30° C. in 5 minutes. The reaction mixture is poured into a mixture of 20 ml. of cool saturated sodium bicarbonate solution and 30 ml. of ether. The ethereal solution is washed with an additional 20 ml. of saturated sodium bicarbonate solution, dried over anhydrous sodium sulfate and filtered. The ether is removed to provide a yellow solid. The solid is recrystallized from acetonitrile to give 259 mg. of the desired product as yellow crystals, mp. 182°–184° C.

EXAMPLE 15

9,10-Anthracenedicarboxaldehyde

Oxygen is bubbled through a solution of 400 mg. of lithium bromide in 20 ml. of acetonitrile for 10 minutes. Then, 240 mg. of the product of Example 2 is added to the acetonitrile solution with stirring. The reaction mixture is kept under oxygen and stirred at 60° C. for 22 hours. The acetonitrile is then removed under reduced pressure to give an orange residue. The residue is washed with water to give 220 mg. of the desired crude product, mp. 225°–230° C.

EXAMPLE 16

9,10-Anthracenedicarboxaldehyde

To a solution of 240 mg. of the product of Example 2 (prepared as described) in 15 ml. of acetonitrile is added a solution of 0.30 ml. of triethylamine in 5 ml. of acetonitrile. The reaction mixture is stirred at room temperature for 4 hours then is cooled in an ice bath. The precipitate is collected by filtration to give 136 mg. of the desired crude product as orange crystals, mp. 224°–228° C.

EXAMPLE 17

1',5'-Dichloro-dispiro[oxirane-2,9'(10'H)-anthracene-10',2''-oxirane]

A solution comprising 18.3 g. of trimethylsulfonium iodide in 150 ml. of dry dimethylsulfoxide is added dropwise, over 25 minutes, to a stirred mixture of 4.31 g. of sodium hydride (50% oil dispersion) and 11.08 g. of 1,5-dichloroanthraquinone in 250 ml. of dry dimethylsulfoxide in the dark under nitrogen. The reaction mixture is stirred at room temperature for two more hours and filtered through a sintered glass funnel. The filtrate is poured into 700 ml. of ice-water and allowed to stand for 20 minutes. The solid is collected and washed with water and methanol, giving 10.5 g. of the desired product as a pale yellow solid, mp. 172°–178° C.

EXAMPLE 18

1,5-Dichloro-9,10-dihydro-9,10-anthracenedicarboxaldehyde

To a solution of 0.1 ml. of boron fluoride etherate in 100 ml. of anhydrous toluene is added 500 mg. of 1',5'-dichloro-dispiro[oxirane-2,9'(10'H)-anthracene-10',2''oxirane]. The mixture is stirred at room temperature for 6 hours and filtered. The filtrate is washed twice with 10 ml. portions of a mixture of 10 ml. of saturated sodium bicarbonate and 10 ml. of ice water, dried over anhydrous sodium sulfate and filtered. The toluene is removed by water pump evacuation at 30° C. to give 0.5 g. of the desired product as a pale yellow solid, mp. 160°–172° C.

We claim:

1. A process for the preparation of 9,10-anthracenedicarboxaldehydes of the formula:

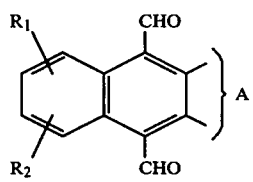

wherein A is a divalent moiety selected from the group consisting of those of the formulae:

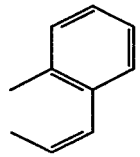 , 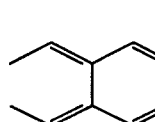 and 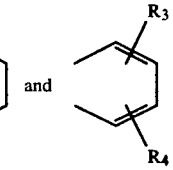

and $R_1$, $R_2$, $R_3$ and $R_4$ are each individually selected from the group consisting of hydrogen, halogen, hydroxy, nitro, amino, sulfonamido, alkyl having up to 4 carbon atoms and alkoxy having up to 4 carbon atoms which comprises rearranging a dispiro[oxirane-2,9'(10'H)-anthracene-10',2''-oxirane] of the formula:

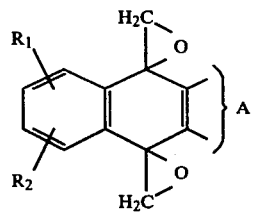

wherein A, $R_1$, $R_2$, $R_3$ and $R_4$ are as hereinabove defined with lithium bromide, lithium perchlorate, boron trifluoride, magnesium bromide, trifluoroacetic acid or methanesulfonic acid in an aprotic organic solvent at 25°–74° C. in the dark for a period of time sufficient for a substantial degree of rearrangement to occur forming an intermediate 9-formyl-10-hydroxymethylanthracene of the formula:

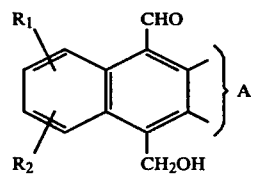

wherein A, $R_1$, $R_2$, $R_3$ and $R_4$ are as hereinabove defined and oxidizing said intermediate with 2–8 mole equivalents of an oxidizing agent in an inert solvent at 0°–100° C. for a period of time sufficient for a substantial degree of oxidation to occur.

2. A process for the preparation of 9,10-anthracenedicarboxaldehydes of the formula:

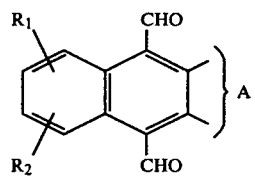

wherein A is a divalent moiety selected from the group consisting of those of the formulae:

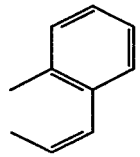 , 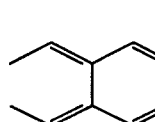 and 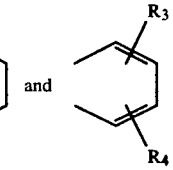

and $R_1$, $R_2$, $R_3$ and $R_4$ are each individually selected from the group consisting of hydrogen, halogen, hydroxy, nitro, amino, sulfonamido, alkyl having up to 4 carbon atoms and alkoxy having up to 4 carbon atoms which comprises rearranging a dispiro[oxirane-2,9'(10'H)-anthracene-10',2''-oxirane] of the formula:

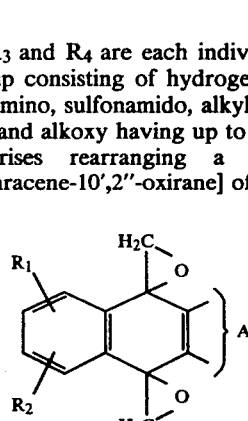

wherein A, $R_1$, $R_2$, $R_3$ and $R_4$ are as hereinabove defined with boron trifluoride, magnesium bromide, trifluoroacetic acid or methanesulfonic acid in an aprotic organic solvent at −45°–0° C. in the presence of base for a period of time sufficient for a substantial degree of rearrangement to occur forming an intermediate 9,10-dihydro-9,10-anthracenedicarboxaldehyde of the formula:

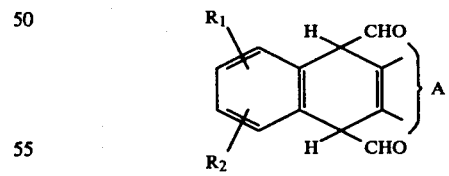

wherein A, $R_1$, $R_2$, $R_3$ and $R_4$ are as hereinabove defined and oxidizing said intermediate with 2–8 mole equivalents of an oxidizing agent in an inert solvent at 0°–100° C. for a period of time sufficient for a substantial degree of oxidation to occur.

* * * * *